US008211434B2

(12) United States Patent
Stern et al.

(10) Patent No.: US 8,211,434 B2
(45) Date of Patent: Jul. 3, 2012

(54) KLK-13 ANTIBODY INHIBITOR FOR TREATING DRY EYE

(75) Inventors: Michael E. Stern, Mission Viejo, CA (US); Karyn F. Siemasko, Irvine, CA (US); Christopher Schaumburg, Irvine, CA (US); Jianping Gao, Irvine, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 13/129,436

(22) PCT Filed: Nov. 23, 2009

(86) PCT No.: PCT/US2009/065561
§ 371 (c)(1),
(2), (4) Date: May 16, 2011

(87) PCT Pub. No.: WO2010/062857
PCT Pub. Date: Jun. 3, 2010

(65) Prior Publication Data
US 2011/0223170 A1 Sep. 15, 2011

Related U.S. Application Data

(60) Provisional application No. 61/118,341, filed on Nov. 26, 2008.

(51) Int. Cl.
*A61K 39/395* (2006.01)
*C07K 16/40* (2006.01)

(52) U.S. Cl. .............. 424/146.1; 424/133.1; 424/136.1; 424/178.1; 530/388.26; 530/387.3; 530/391.1; 530/389.1

(58) Field of Classification Search .................. None
See application file for complete search history.

(56) References Cited

U.S. PATENT DOCUMENTS

| | | | |
|---|---|---|---|
| 4,676,980 A | 6/1987 | Segal et al. | |
| 4,816,567 A | 3/1989 | Cabilly et al. | |
| 5,229,275 A | 7/1993 | Goroff | |
| 5,545,806 A | 8/1996 | Lonberg et al. | |
| 5,545,807 A | 8/1996 | Surani et al. | |
| 5,565,332 A | 10/1996 | Hoogenboom et al. | |
| 5,567,610 A | 10/1996 | Borrebaeck et al. | |
| 5,569,825 A | 10/1996 | Lonberg et al. | |
| 5,571,894 A | 11/1996 | Wels et al. | |
| 5,573,905 A | 11/1996 | Lerner et al. | |
| 5,587,458 A | 12/1996 | King et al. | |
| 5,591,669 A | 1/1997 | Krimpenfort et al. | |
| 5,641,870 A | 6/1997 | Rinderknecht et al. | |
| 5,731,168 A | 3/1998 | Carter et al. | |
| 5,739,277 A | 4/1998 | Presta et al. | |
| 5,821,337 A | 10/1998 | Carter et al. | |
| 5,837,234 A | 11/1998 | Gentile et al. | |
| 5,869,046 A | 2/1999 | Presta et al. | |
| 6,331,427 B1 | 12/2001 | Robison | |
| 2007/0212362 A1 | 9/2007 | Filvaroff | |
| 2007/0269428 A1 | 11/2007 | Christie et al. | |
| 2008/0095775 A1 | 4/2008 | Lewis et al. | |
| 2008/0221307 A1 | 9/2008 | Tocker et al. | |
| 2008/0269467 A1 | 10/2008 | Allan et al. | |

FOREIGN PATENT DOCUMENTS

| | | |
|---|---|---|
| WO | 91/00360 | 1/1991 |
| WO | 92/20373 | 11/1992 |
| WO | 93/08829 | 5/1993 |
| WO | 93/16185 | 8/1993 |
| WO | 94/04690 | 3/1994 |
| WO | 96/16673 | 6/1996 |
| WO | 97/17852 | 5/1997 |
| WO | 98/02463 | 1/1998 |
| WO | 01/94629 | 12/2001 |
| WO | 03/038129 | 5/2003 |

OTHER PUBLICATIONS

Barabino et al. Animal models of dry eye: a critical assessment of opportunities and limitations. Invest Ophthalmol Vis Sci. Jun. 2004;45(6):1641-6.*
Brennan et al., *Science*, 229:81 (1985).
Bruggemann et al., *Year in Immuno.* 7:33 (1993).
Caron et al., *J. Exp Med.* 176:1191-1195 (1992).
Carter et al., *Proc. Natl. Acad. Sci. USA*, 89:4285 (1992).
Carter et al., *Bio/Technology* 10: 163-167 (1992)).
Chang et al. *Br. J. Cancer*, 86(9):1457-64 (2002).
Chothia et al., *J. Mol. Biol.*, 196:901 (1987).
Clackson et al. , *Nature*, 352:624-628 (1991).
Y. Danjo, et al., *Invest Ophthalmol Vis Sci*, 39:2602-2609 (1998).
Goding, *Monoclonal Antibodies: Principles and Practice*, pp. 59-103 (Academic Press, 1986)).
Griffith et al., *EMBO J.* 12:725-734 (1993).
Gruber et al., *J. Immunol.*, 152:5368 (1994).
Hollinger et al., *Proc. Natl. Acad. Sci. USA* 90:6444-6448 (1993).
Jones et al., Nature, 321:522-525 (1986).
Jakobovits et al., *Proc. Natl. Acad. Sci. USA*, 90:2551 (1993).
Jakobovits et al., *Nature*, 362:255-258 (1993).
Johnson, Kevin S. and Chiswell, David J., *Current Opinion in Structural Biology* 3:564-571 (1993).
Kohler et al., *Nature*, 256:495 (1975).
Kostelny et al., *J. Immunol.* 148(5): 1547-1553 (1992).
Kozbor, *J. Immunol.*, 133:3001 (1984). G. Langer, et al., *Invest Ophthalmol Vis Sci*, 40:2220-2224 (1999).
McCafferty et al., *Nature*, 348:552-554 (1990).
Marks et al., *J. Mol. Biol.*, 222:581-597 (1991).
Marks et al., *Bio/Technology*, 10:779-783 (1992).
Millstein et al., *Nature* 305:537-539 (1983).
Morimoto et al., *Journal of Biochemical and Biophysical Methods* 24:107-117 (1992).
Morrison, et al., *Proc. Natl. Acad. Sci. USA*, 81:6851 (1984).
F.P. Paulson, et al., *Invest Ophthalmol Vis Sci*, 43 :3359-3364 (2002).
Pluckthun, *Immunol. Revs.* 130:151-188 (1992).
Presta, *Curr. Op. Struct. Biol.*, 2:593-596 (1992).
Presta et al., *J. Immunol.* 151:2623 (1993).
Riechmann et al., *Nature*, 332:323-329 (1988).
Remington's Pharmaceutical Sciences 16th edition, Osol, A. Ed. (1980).
Shopes, B. *J. Immunol.* 148:2918-2922 (1992).
Sims et al., *J. Immunol.* 151:2296 (1993).
Skerra et al., *Curr. Opinion in Immunol.*, 5:256-262 (1993).
Stevenson et al., *Anti-Cancer Drug Design* 3:219-230 (1989).
Suresh et al., *Methods in Enzymology* 121:210 (1986).
Traunecker et al., *EMBO J.* 10:3655-3659 (1991).
Verhoeyen et al., *Science*, 239:1534-1536 (1988).
Waterhouse et al., *Nuc. Acids. Res.* 21:2265-2266 (1993).
G. M. Yousef et al. *J. Biol. Chem.*, 275:11891-11898 (2000).

* cited by examiner

*Primary Examiner* — David Romeo
(74) *Attorney, Agent, or Firm* — Joel B. German; Debra D. Condino; Allergan, Inc.

(57) ABSTRACT

Disclosed herein is a method of treating dry eye with a KLK-13 antibody.

2 Claims, 6 Drawing Sheets

KLK-13 ANTIBODY INHIBITOR FOR TREATING DRY EYE

CROSS-REFERENCE

Figure 1:
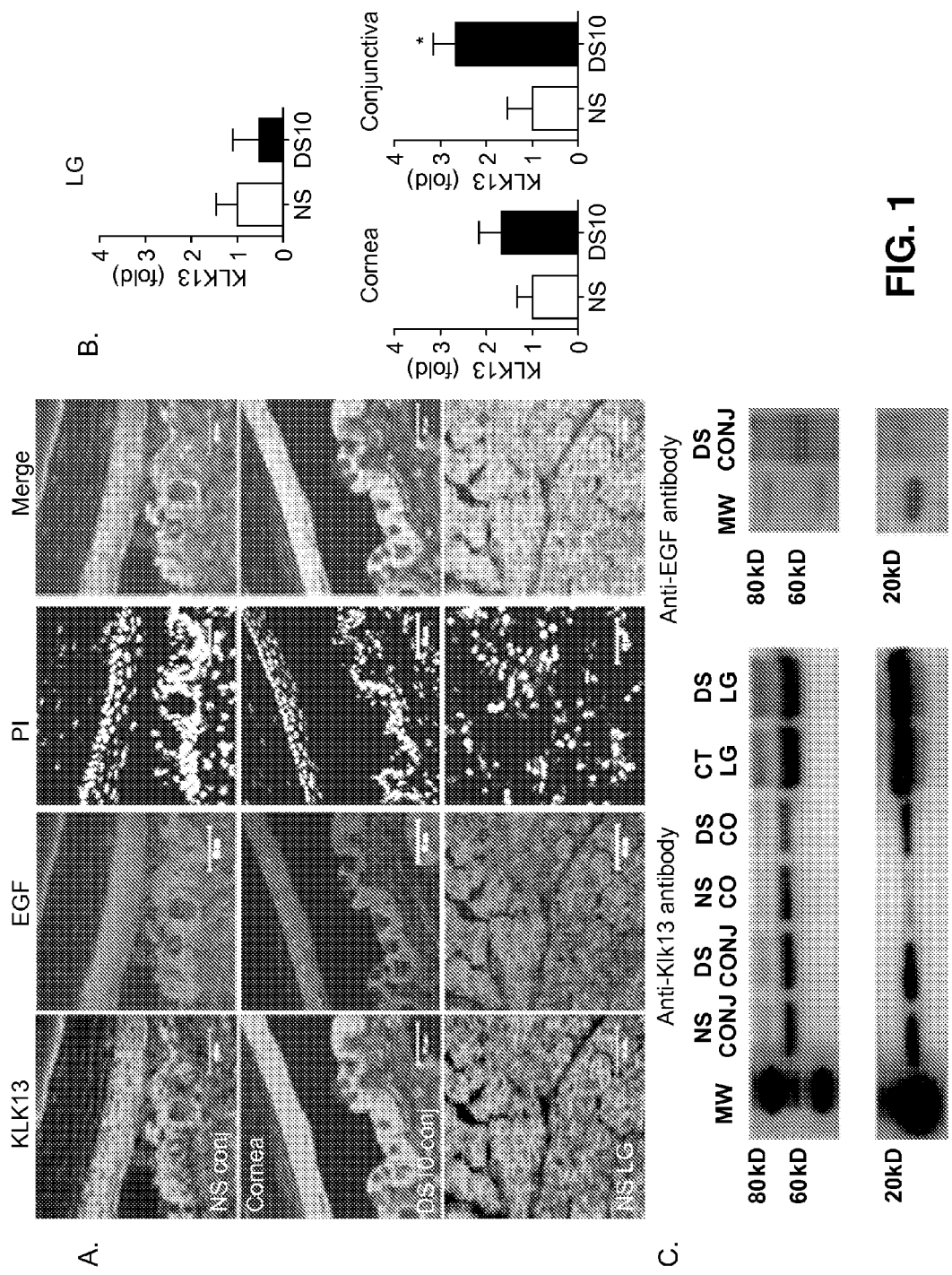

This application claims the benefit of U.S. Provisional Patent Application Ser. No. 61/118,341, filed on Nov. 26, 2008, the entire disclosure of which is incorporated herein by this specific reference.

Disclosed herein are methods for treating dry eye by topically administering an antibody that binds KLK-13.

DETAILED DESCRIPTION OF THE INVENTION

Dry Eye

Dry eye disease is a general term for a variety of conditions caused by abnormalities in the tear film. Dry eye is characterized by symptoms such as a sandy-gritty feeling in the eye, burning, irritation, or a foreign-body sensation that worsens during the day. Patients suffering from dry eye disease complain of mild to severe symptoms, and those with severe symptoms may experience constant and disabling eye irritation, and develop ocular surface epithelial disease and sight-threatening sterile or microbial corneal ulceration.

The tear film consists of an inner mucous layer, a middle aqueous layer which forms the bulk of the tear film, and an outer lipid layer. The aqueous layer is secreted by the lacrimal gland and the accessory lacrimal glands, and the tear fluid is drained by the efferent tear ducts. While the underlying causes of dry eye diseases are largely unknown, it is generally accepted that they are associated with abnormalities in the tear composition or flow, which are affected by a variety of factors including aqueous layer secretion through lacrimal gland and drainage through the efferent tear passage. In addition to abnormalities in the lacrimal glands, abnormalities in the meibomian glands (which secrete the lipid layer), and abnormalities in drainage through the efferent tear duct passage, changes in mucin composition and mucous viscosity may also affect tear flow. G. Langer, et al., *Invest Ophthalmol Vis Sci*, 40:2220-2224 (1999), Y. Danjo, et al., *Invest Ophthalmol Vis Sci*, 39:2602-2609 (1998), and F. P. Paulson, et al., *Invest Ophthalmol Vis Sci*, 43:3359-3364 (2002).

Until recently, the only methods used to treat dry eye disease were topical administration of over-the-counter compositions that serve as artificial tears (such as Refresh®, marketed by Allergan, Inc.), or surgery to close efferent drainage. Recently, a topical ophthalmic product containing Cyclosporin A, marketed by Allergan Inc., as Restasis®, was introduced, which has shown to be effective in treating many cases of dry eye. However, to maximize the number of options available to the physician and the patient any new and effective treatment for dry eye disease is highly desirable.

The inventors have discovered that a composition comprising an anti-KLK-13 antibody may be administered topically to the eye to increase tear production and treat dry eye.

KLK-13

KLK13 is a member of the group of protease enzymes, and is described in WO03038129, WO0194629, and U.S. Pat. No. 6,331,427, the disclosures of which are incorporated herein by reference.

Kallikreins, a subgroup of serine proteases with a molecular weight of 25,000-40,000, have diverse physiologic functions in many tissues. They have the ability to release vasoactive peptides from kininogen in vitro, although the kininogenase activity of different kallikreins is highly variable. The true physiologic role of specific kallikreins is often unrelated to the kininogenase activity. In the mouse a major site of kallikrein synthesis is the male submaxillary gland. Glandular kallikreins are also synthesized in the pancreas and kidney. The several kallikreins found in this tissue include epidermal growth factor binding protein (EGF-BP) and the gamma subunit of nerve growth factor (NGFG) which are responsible for the processing of EGF and NGF, respectively. Although EGF-BP and NGFG exhibit strict substrate specificity, they share extensive amino acid sequence homology and immunologic crossreactivity. Mason et al. (1983) concluded that the glandular kallikrein gene family comprises 25-30 highly homologous genes that encode specific proteases involved in the processing of biologically active peptides.

Using the positional candidate gene approach, G. M. Yousef et al. identified a new member of the kallikrein gene family, KLK13, which they called KLKL4, in a 300-kb region on chromosome 19q13.3-q13.4, where other known kallikrein genes are localized. *J. Biol. Chem.*, 275:11891-11898 (2000). KLK13 contains 5 coding exons and is subject to alternative splicing. It exists in 2 main forms: a long form that encodes a deduced 277-amino acid protein with a predicted molecular mass of 30.6 kD), and a short form, referred to as the short KLKL4 variant, that utilizes an upstream alternative splice donor site located in exon 3 that generates a truncated protein. The KLK13 protein shares 51% amino acid identity with KLK11 and KLK6. RT-PCR analysis showed that the KLK13 protein is primarily expressed in mammary gland, prostate, salivary gland, and testis. Lower levels of expression are found in many other tissues. Yousef et al. determined that the KLK13 gene is regulated by steroid hormones in a human breast cancer cell line. They presented data suggesting that KLK13 is downregulated, at the mRNA level, in breast cancer tissues and breast cancer cell lines. Chang et al. concluded that KLK13 expression, as assessed by quantitative reverse transcriptase-polymerase chain reaction, is an independent favourable prognostic marker for breast carcinoma. *Br. J. Cancer*, 86(9):1457-64 (2002).

KLK-13 Antibodies

In one embodiment, one can use in the method of the invention an antibody or functional fragment thereof which binds KLK-13. Such antibodies and fragments are well known in the art, and are described in, for example, U.S. Patent Application Publication No. 2008/0269467, U.S. Patent Application Publication No. 2008/0221307, U.S. Patent No. 2008/0095775, U.S. Patent Application Publication No. 2007/0269428, and U.S. Patent Application Publication No. 2007/0212362.

Antibodies useful in the method of the invention include polyclonal, monoclonal, humanized, bispecific, and heteroconjugate antibodies, and functional fragments thereof.

Polyclonal Antibodies

Polyclonal antibodies may be raised in animals by multiple subcutaneous (sc) or intraperitoneal (ip) injections of the relevant antigen and an adjuvant. It may be useful to conjugate the relevant antigen (especially when synthetic peptides are used) to a protein that is immunogenic in the species to be immunized. For example, the antigen can be conjugated to keyhole limpet hemocyanin (KLH), serum albumin, bovine thyroglobulin, or soybean trypsin inhibitor, using a bifunctional or derivatizing agent, e.g., maleimidobenzoyl sulfosuccinimide ester (conjugation through cysteine residues), N-hydroxysuccinimide (through lysine residues), glutaraldehyde, succinic anhydride, $SOCl_2$, or $R_1N=C=NR$, where R and $R_1$ are different alkyl groups.

Animals can be immunized against the antigen, immunogenic conjugates, or derivatives by combining, e.g., 100 µg or 5 μg of the protein or conjugate (for rabbits or mice, respectively) with 3 volumes of Freund's complete adjuvant and injecting the solution intradermally at multiple sites. One month later, the animals are boosted with 1/5 to 1/10 the original amount of peptide or conjugate in Freund's complete adjuvant by subcutaneous injection at multiple sites. Seven to 14 days later, the animals are bled and the serum is assayed for antibody titer. Animals are boosted until the titer plateaus. Conjugates also can be made in recombinant cell culture as protein fusions. Also, aggregating agents such as alum are suitably used to enhance the immune response.

Monoclonal Antibodies

Monoclonal antibodies may be made using the hybridoma method first described by Kohler et al., *Nature*, 256:495 (1975), or may be made by recombinant DNA methods (U.S. Pat. No. 4,816,567, the disclosure of which is incorporated herein by reference).

In the hybridoma method, a mouse or other appropriate host animal, such as a hamster, is immunized as described above to elicit lymphocytes that produce or are capable of producing antibodies that will specifically bind to the protein used for immunization. Alternatively, lymphocytes may be immunized in vitro. After immunization, lymphocytes are isolated and then fused with a myeloma cell line using a suitable fusing agent, such as polyethylene glycol, to form a hybridoma cell (Goding, *Monoclonal Antibodies: Principles and Practice*, pp. 59-103 (Academic Press, 1986)).

The hybridoma cells thus prepared are seeded and grown in a suitable culture medium which medium preferably contains one or more substances that inhibit the growth or survival of the unfused, parental myeloma cells (also referred to as fusion partner). For example, if the parental myeloma cells lack the enzyme hypoxanthine guanine phosphoribosyl transferase (HGPRT or HPRT), the selective culture medium for the hybridomas typically will include hypoxanthine, aminopterin, and thymidine (HAT medium), which substances prevent the growth of HGPRT-deficient cells.

Preferred fusion partner myeloma cells are those that fuse efficiently, support stable high-level production of antibody by the selected antibody-producing cells, and are sensitive to a selective medium that selects against the unfused parental cells. Preferred myeloma cell lines are murine myeloma lines, such as those derived from MOPC-21 and MPC-11 mouse tumors available from the Salk Institute Cell Distribution Center, San Diego, Calif. USA, and SP-2 and derivatives e.g., X63-Ag8-653 cells available from the American Type Culture Collection, Manassas, Va., USA. Human myeloma and mouse-human heteromyeloma cell lines also have been described for the production of human monoclonal antibodies (Kozbor, *J. Immunol.*, 133:3001 (1984); and Brodeur et al., *Monoclonal Antibody Production Techniques and Applications*, pp. 51-63 (Marcel Dekker, Inc., New York, 1987)).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunosorbent assay (ELISA).

The binding affinity of the monoclonal antibody can, for example, be determined by the Scatchard analysis described in Munson et al., Anal. Biochem., 107:220 (1980).

Once hybridoma cells that produce antibodies of the desired specificity, affinity, and/or activity are identified, the clones may be subcloned by limiting dilution procedures and grown by standard methods (Goding, *Monoclonal Antibodies: Principles and Practice*, pp. 59-103 (Academic Press, 1986)). Suitable culture media for this purpose include, for example, D-MEM or RPMI-1640 medium. In addition, the hybridoma cells may be grown in vivo as ascites tumors in an animal e.g, by i.p. injection of the cells into mice.

The monoclonal antibodies secreted by the subclones are suitably separated from the culture medium, ascites fluid, or serum by conventional antibody purification procedures such as, for example, affinity chromatography (e.g., using protein A or protein G-Sepharose) or ion-exchange chromatography, hydroxylapatite chromatography, gel electrophoresis, dialysis, etc.

DNA encoding the monoclonal antibodies is readily isolated and sequenced using conventional procedures (e.g., by using oligonucleotide probes that are capable of binding specifically to genes encoding the heavy and light chains of murine antibodies). The hybridoma cells serve as a preferred source of such DNA. Once isolated, the DNA may be placed into expression vectors, which are then transfected into host cells such as *E. coli* cells, simian COS cells, Chinese Hamster Ovary (CHO) cells, or myeloma cells that do not otherwise produce antibody protein, to obtain the synthesis of monoclonal antibodies in the recombinant host cells. Review articles on recombinant expression in bacteria of DNA encoding the antibody include Skerra et al., *Curr. Opinion in Immunol.*, 5:256-262 (1993) and Pluckthun, *Immunol. Revs.* 130: 151-188 (1992).

In a further embodiment, monoclonal antibodies or antibody fragments can be isolated from antibody phage libraries generated using the techniques described in McCafferty et al., *Nature*, 348:552-554 (1990). Clackson et al., *Nature*, 352: 624-628 (1991) and Marks et al., *J. Mol. Biol.*, 222:581-597 (1991) describe the isolation of murine and human antibodies, respectively, using phage libraries. Subsequent publications describe the production of high affinity (nM range) human antibodies by chain shuffling (Marks et al., *Bio/Technology*, 10:779-783 (1992)), as well as combinatorial infection and in vivo recombination as a strategy for constructing very large phage libraries (Waterhouse et al., *Nuc. Acids. Res.* 21:2265-2266 (1993)). Thus, these techniques are viable alternatives to traditional monoclonal antibody hybridoma techniques for isolation of monoclonal antibodies.

The DNA that encodes the antibody may be modified to produce chimeric or fusion antibody polypeptides, for example, by substituting human heavy chain and light chain constant domain ($C_H$ and $C_L$) sequences for the homologous murine sequences (U.S. Pat. No. 4,816,567, the disclosure of which is incorporated herein by reference; and Morrison, et al., *Proc. Natl. Acad. Sci. USA*, 81:6851 (1984)), or by fusing the immunoglobulin coding sequence with all or part of the coding sequence for a non-immunoglobulin polypeptide (heterologous polypeptide). The non-immunoglobulin polypeptide sequences can substitute for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

Human and Humanized Antibodies

The anti-KLK-13 antibodies of the invention may further comprise humanized antibodies or human antibodies. Humanized forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., Nature, 321:522-525 (1986); Riechmann et al., Nature, 332:323-329 (1988); and Presta, Curr. Op. Struct. Biol., 2:593-596 (1992)].

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers [Jones et al., Nature, 321:522-525 (1986); Riechmann et al., Nature 332:323-327 (1988); Verhoeyen et al., Science, 239:1534-1536 (1988)], by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is very important to reduce antigenicity and HAMA response (human anti-mouse antibody) when the antibody is intended for human therapeutic use. According to the so-called "best fit" method, the sequence of the variable domain of a rodent antibody is screened against the entire library of known human variable domain sequences. The human V domain sequence which is closest to that of the rodent is identified and the human framework region (FR) within it accepted for the humanized antibody (Sims et al., J. Immunol. 151:2296 (1993); Chothia et al., J. Mol. Biol., 196:901 (1987)). Another method uses a particular framework region derived from the consensus sequence of all human antibodies of a particular subgroup of light or heavy chains. The same framework may be used for several different humanized antibodies (Carter et al., Proc. Natl. Acad. Sci. USA, 89:4285 (1992); Presta et al., J. Immunol. 151:2623 (1993)).

It is further important that antibodies be humanized with retention of high binding affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

Various forms of a humanized anti-KLK-13 antibody are contemplated. For example, the humanized antibody may be an antibody fragment, such as a Fab, which is optionally conjugated with one or more cytotoxic agent(s) in order to generate an immunoconjugate. Alternatively, the humanized antibody may be an intact antibody, such as an intact IgG1 antibody.

As an alternative to humanization, human antibodies can be generated. For example, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array into such germ-line mutant mice will result in the production of human antibodies upon antigen challenge. See, e.g., Jakobovits et al., Proc. Natl. Acad. Sci. USA, 90:2551 (1993); Jakobovits et al., Nature, 362:255-258 (1993); Bruggemann et al., Year in Immuno. 7:33 (1993); U.S. Pat. Nos. 5,545,806, 5,569,825, 5,591,669; U.S. Pat. No. 5,545,807; and WO 97/17852 (the disclosures of the foregoing patent references are incorporated by reference herein).

Alternatively, phage display technology (McCafferty et al., Nature 348:552-553 [1990]) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B-cell. Phage display can be performed in a variety of formats, reviewed in, e.g., Johnson, Kevin S. and Chiswell, David J., Current Opinion in Structural Biology 3:564-571 (1993). Several sources of V-gene segments can be used for phage display. Clackson et al., Nature, 352:624-628 (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Marks et al., J. Mol. Biol. 222:581-597 (1991), or Griffith et al., EMBO J. 12:725-734 (1993). See, also, U.S. Pat. Nos. 5,565,332 and 5,573,905.

As discussed above, human antibodies may also be generated by in vitro activated B cells (see U.S. Pat. Nos. 5,567,610 and 5,229,275, incorporated herein by reference).

Antibody Fragments

Various techniques have been developed for the production of antibody fragments. Traditionally, these fragments were derived via proteolytic digestion of intact antibodies (see, e.g., Morimoto et al., *Journal of Biochemical and Biophysical Methods* 24:107-117 (1992); and Brennan et al., *Science*, 229:81 (1985)). However, these fragments can now be produced directly by recombinant host cells. Fab, Fv and ScFv antibody fragments can all be expressed in and secreted from *E. coli*, thus allowing the facile production of large amounts of these fragments. Antibody fragments can be isolated from the antibody phage libraries discussed above. Alternatively, Fab'-SH fragments can be directly recovered from *E. coli* and chemically coupled to form $F(ab')_2$ fragments (Carter et al., *Bio/Technology* 10: 163-167 (1992)). According to another approach, $F(ab')_2$ fragments can be isolated directly from recombinant host cell culture. Fab and $F(ab')_2$ fragment with increased in vivo half-life comprising a salvage receptor binding epitope residues are described in U.S. Pat. No. 5,869,046. Other techniques for the production of antibody fragments will be apparent to the skilled practitioner. In other embodiments, the antibody of choice is a single chain Fv fragment (scFv). See WO 93/16185; U.S. Pat. No. 5,571,894; and U.S. Pat. No. 5,587,458, the disclosures of which are incorporated by reference. Fv and sFv are the only species with intact combining sites that are devoid of constant regions; thus, they are suitable for reduced nonspecific binding during in vivo use. sFv fusion proteins may be constructed to yield fusion of an effector protein at either the amino or the carboxy terminus of an sFv. See Antibody Engineering, ed. Borrebaeck, supra. The antibody fragment may also be a "linear antibody", e.g., as described in U.S. Pat. No. 5,641,870 for example, the disclosure of which is incorporated by reference. Such linear antibody fragments may be monospecific or bispecific.

Bispecific Antibodies

Bispecific antibodies are antibodies that have binding specificities for at least two different epitopes. Exemplary bispecific antibodies may bind to two different epitopes of KLK-13. Other such antibodies may combine a KLK-13 binding site with a binding site for another polypeptide. Alternatively, an anti-KLK-13 antibody arm may be combined with an arm which binds to a triggering molecule on a leukocyte such as a T-cell receptor molecule (e.g. CD3), or Fc receptors for IgG (FcγR), such as FcγRI (CD64), FcγRII (CD32) and FcγRIII (CD16), so as to focus and localize cellular defense mechanisms to the KLK-13-expressing and/or binding cell. Bispecific antibodies may also be used to localize cytotoxic agents to cells which express and/or bind KLK-13. These antibodies possess a KLK-13 binding arm and an arm which binds the cytotoxic agent (e.g., saporin, anti-interferon-α, vinca alkaloid, ricin A chain, methotrexate or radioactive isotope hapten). Bispecific antibodies can be prepared as full length antibodies or antibody fragments (e.g., $F(ab')_2$ bispecific antibodies).

WO 96/16673 describes a bispecific anti-ErbB2/anti-FcγRIII antibody and U.S. Pat. No. 5,837,234 discloses a bispecific anti-ErbB2/anti-FcγRI antibody. A bispecific anti-ErbB2/Fcγ antibody is shown in WO98/02463. U.S. Pat. No. 5,821,337 teaches a bispecific anti-ErbB2/anti-CD3 antibody. The disclosures of all of these references are incorporated herein by reference.

Methods for making bispecific antibodies are known in the art. Traditional production of full length bispecific antibodies is based on the co-expression of two immunoglobulin heavy chain-light chain pairs, where the two chains have different specificities (Millstein et al., *Nature* 305:537-539 (1983)). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, the disclosure of which is incorporated by reference, and in Traunecker et al., *EMBO J.* 10:3655-3659 (1991).

According to a different approach, antibody variable domains with the desired binding specificities (antibody-antigen combining sites) are fused to immunoglobulin constant domain sequences. Preferably, the fusion is with an Ig heavy chain constant domain, comprising at least part of the hinge, $C_H2$, and $C_H3$ regions. It is preferred to have the first heavy-chain constant region ($C_H1$) containing the site necessary for light chain bonding, present in at least one of the fusions. DNAs encoding the immunoglobulin heavy chain fusions and, if desired, the immunoglobulin light chain, are inserted into separate expression vectors, and are co-transfected into a suitable host cell. This provides for greater flexibility in adjusting the mutual proportions of the three polypeptide fragments in embodiments when unequal ratios of the three polypeptide chains used in the construction provide the optimum yield of the desired bispecific antibody. It is, however, possible to insert the coding sequences for two or all three polypeptide chains into a single expression vector when the expression of at least two polypeptide chains in equal ratios results in high yields or when the ratios have no significant affect on the yield of the desired chain combination.

In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., *Methods in Enzymology* 121:210 (1986).

According to another approach described in U.S. Pat. No. 5,731,168 (incorporated herein by reference), the interface between a pair of antibody molecules can be engineered to maximize the percentage of heterodimers which are recovered from recombinant cell culture. The preferred interface comprises at least a part of the $C_H3$ domain. In this method, one or more small amino acid side chains from the interface of the first antibody molecule are replaced with larger side chains (e.g., tyrosine or tryptophan). Compensatory "cavities" of identical or similar size to the large side chain(s) are created on the interface of the second antibody molecule by replacing large amino acid side chains with smaller ones (e.g., alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., *Science* 229:81 (1985) describe a procedure wherein intact antibodies are proteolytically cleaved to generate F(ab')$_2$ fragments. These fragments are reduced in the presence of the dithiol complexing agent, sodium arsenite, to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Recent progress has facilitated the direct recovery of Fab'-SH fragments from *E. coli*, which can be chemically coupled to form bispecific antibodies. Shalaby et al., *J. Exp. Med.* 175: 217-225 (1992) describe the production of a fully humanized bispecific antibody F(ab')$_2$ molecule. Each Fab' fragment was separately secreted from *E. coli* and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets. Various techniques for making and isolating bispecific antibody fragments directly from recombinant cell culture have also been described. For example, bispecific antibodies have been produced using leucine zippers. Kostelny et al., *J. Immunol.* 148(5): 1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., *Proc. Natl. Acad. Sci. USA* 90:6444-6448 (1993) has provided an alternative mechanism for making bispecific antibody fragments. The fragments comprise a $V_H$ connected to a $V_L$ by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See Gruber et al., *J. Immunol.*, 152:5368 (1994).

Antibodies with more than two valencies are contemplated. For example, trispecific antibodies can be prepared. Tutt et al., *J. Immunol.* 147:60 (1991).

Heteroconjugate Antibodies

Heteroconjugate antibodies are also within the scope of the present invention. Heteroconjugate antibodies are composed of two covalently joined antibodies. Such antibodies have, for example, been proposed to target immune system cells to unwanted cells [U.S. Pat. No. 4,676,980], and for treatment of HIV infection [WO 91/00360; WO 92/200373; EP 03089]. It is contemplated that the antibodies may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

Multivalent Antibodies

A multivalent antibody may be internalized (and/or catabolized) faster than a bivalent antibody by a cell expressing an antigen to which the antibodies bind. The antibodies of the present invention can be multivalent antibodies (which are other than of the IgM class) with three or more antigen binding sites (e.g. tetravalent antibodies), which can be readily produced by recombinant expression of nucleic acid encoding the polypeptide chains of the antibody. The multivalent antibody can comprise a dimerization domain and three or more antigen binding sites. The preferred dimerization domain comprises (or consists of) an Fc region or a hinge region. In this scenario, the antibody will comprise an Fc region and three or more antigen binding sites amino-terminal to the Fc region. The preferred multivalent antibody herein comprises (or consists of) three to about eight, but preferably four, antigen binding sites. The multivalent antibody comprises at least one polypeptide chain (and preferably two polypeptide chains), wherein the polypeptide chain(s) comprise two or more variable domains. For instance, the polypeptide chain(s) may comprise VD1-(X1)$_n$-VD2-(X2)$_n$-Fc, wherein VD1 is a first variable domain, VD2 is a second variable domain, Fc is one polypeptide chain of an Fc region, X1 and X2 represent an amino acid or polypeptide, and n is 0 or 1. For instance, the polypeptide chain(s) may comprise: VH-CH1-flexible linker-VH-CH1-Fc region chain; or VH-CH1-VH-CH1-Fc region chain. The multivalent antibody herein preferably further comprises at least two (and preferably four) light chain variable domain polypeptides. The multivalent antibody herein may, for instance, comprise from about two to about eight light chain variable domain polypeptides. The light chain variable domain polypeptides contemplated here comprise a light chain variable domain and, optionally, further comprise a CL domain.

Function Engineering

It may be desirable to modify the antibody of the invention with respect to effector function, e.g., so as to enhance antigen-dependent cell-mediated cytotoxicity (ADCC) and/or complement dependent cytotoxicity (CDC) of the antibody. This may be achieved by introducing one or more amino acid substitutions in an Fc region of the antibody. Alternatively or additionally, cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., *J. Exp Med.* 176:1191-1195 (1992) and Shopes, B. *J. Immunol.* 148:2918-2922 (1992). Homodimeric antibodies may also be prepared using heterobifunctional cross-linkers as described in Wolff et al., Cancer Research 53:2560-2565 (1993). Alternatively, an antibody can be engineered which has dual Fc regions and may thereby have enhanced complement lysis and ADCC capabilities. See Stevenson et al., *Anti-Cancer Drug Design* 3:219-230 (1989). To increase the serum half life of the antibody, one may incorporate a salvage receptor binding epitope into the antibody (especially an antibody fragment) as described in U.S. Pat. No. 5,739,277, for example. As used herein, the term "salvage receptor binding epitope" refers to an epitope of the Fc region of an IgG molecule (e.g., IgG$_1$, IgG$_2$, IgG$_3$, or IgG$_4$) that is responsible for increasing the in vivo serum half-life of the IgG molecule.

Formulation

Therapeutic formulations of antibody according to the present invention may be prepared for storage by mixing the antibody having the desired degree of purity with optional physiologically acceptable carriers, excipients or stabilizers (Remington's Pharmaceutical Sciences 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN®, PLURONICS®, or polyethylene glycol (PEG).

In relationship to any of the compositions described herein, it is preferable that an effective amount of buffer be included to maintain the pH from about 6 to about 8, preferably about 7. Buffers used are those known to those skilled in the art, and, while not intending to be limiting, some examples are acetate, borate, carbonate, citrate, and phosphate buffers. Preferably, the buffer comprises borate. An effective amount of buffer necessary for the purposes of this invention can be readily determined by a person skilled in the art without undue experimentation. In cases where the buffer comprises borate, it is preferable that the concentration of the borate buffer be about 0.6%.

In any of the compositions related described herein related to this invention, it is preferable for a tonicity agent to be used. Tonicity agents are used in ophthalmic compositions to adjust the concentration of dissolved material to the desired isotonic range. Tonicity agents are known to those skilled in the ophthalmic art, and, while not intending to be limiting, some examples include glycerin, mannitol, sorbitol, sodium chloride, and other electrolytes. Preferably, the tonicity agent is sodium chloride.

In any of the compositions related to the present invention which are described herein, it is preferable for a preservative to be used when the composition is intended for multiple use. There may also be reasons to use a preservative in single use compositions depending on the individual circumstances. The term preservative has the meaning commonly understood in the ophthalmic art. Preservatives are used to prevent bacterial contamination in multiple-use ophthalmic preparations, and, while not intending to be limiting, examples include benzalkonium chloride, stabilized oxychloro complexes (otherwise known as Purite®), phenylmercuric acetate, chlorobutanol, benzyl alcohol, parabens, and thimerosal. Preferably, the preservative is benzalkonium chloride (BAK).

Under certain circumstances, a surfactant might be used in any of the compositions related to this invention which are described herein. The term surfactant used herein has the meaning commonly understood in the art. Surfactants are used to help solubilize the therapeutically active agent or other insoluble components of the composition, and may serve other purposes as well. Anionic, cationic, amphoteric, zwitterionic, and nonionic surfactants may all be used in this invention. For the purposes of this invention, it is preferable that a nonionic surfactant, such as polysorbates, poloxamers, alcohol ethoxylates, ethylene glycol-propylene glycol block copolymers, fatty acid amides, alkylphenol ethoxylates, or phospholipids, is used in situations where it is desirable to use a surfactant.

Another type of compound that might be used in any composition of this invention described herein is a chelating agent. The term chelating agent refers to a compound that is capable of complexing a metal, as understood by those of ordinary skill in the chemical art. Chelating agents are used in ophthalmic compositions to enhance preservative effectiveness. While not intending to be limiting, some useful chelating agents for the purposes of this invention are edetate salts, like edetate disodium, edetate calcium disodium, edetate sodium, edetate trisodium, and edetate dipotassium.

Administration

One can use any of the compounds described above to treat dry eye. To "treat," as used here, means to deal with medically. It includes administering the compounds of the invention to alleviate symptoms of dry eye, such as inflammation and dryness, as well as to correct the physiological changes associated with dry eye, such as increased proinflammatory cytokine expression, inflammatory cell infiltration, decreased tear production and goblet cell number.

Compositions of the invention are administered topically to the eye. Depending on the type and severity of the disease, about 1 µg/kg to about 50 mg/kg (e.g., 0.1-20 mg/kg) of antibody is an initial candidate dosage for administration to the patient. A typical daily or weekly dosage might range from about 1 µg/kg to about 20 mg/kg or more.

EXAMPLES

The invention is further illustrated by the following examples.

Example I

The inventors hypothesized that Klk13 functions as an autoantigen during the immunopathogenesis of experimental autoimmune lacrimal keratoconjunctivitis (ALKC). To evaluate the role of Klk13 during ALKC they assessed i) Klk13 mRNA and protein expression in the Lacrimal Functional Unit (LFU: cornea, conjunctiva, lacrimal glands, meibomian glands), ii) the Klk13 autoantibody response during ALKC, iii) the capacity of CD4+ T cells from Klk13-immunized mice to respond to ocular surface antigens present in cornea and conjunctiva of ALKC mice and iv) the ability of Klk13 to exacerbate ALKC in vivo.

Female C57BL/6 mice exposed to desiccating stress (DS; subcutaneous scopolamine injections (0.5 mg/0.2 ml) TID, humidity <40%, and continuous air flow) for 10 days. Real time PCR and western blot analysis were used to determine if Klk13 mRNA and protein were expressed in the LFU during experimental ALKC. Serum was also isolated from control mice or those exposed to DS for 10 days to assay for Klk13 autoantibody production. In addition, a co-culture experiment was performed to determine if immunization with Klk13 potentiates the proliferative response of CD4+ T cells from ALKC mice; CD4+ T cells were isolated from the spleen and cervical lymph nodes of Klk13-immunized (10 µg) female C57BL/6 mice exposed to DS for 10 days and mixed with minced cornea and conjunctiva from 10 day DS or control mice. Cells were co-cultured for 4 days and T cell proliferation was measured by WST assay. To further determine if Klk13 contributed to the immunopathogenesis of ALKC mice were exposed to DS for 10 days and topically challenged with Klk13 (1.5 µg/eye on days 7, 8 and 9). On day 10, tear cytokine levels, inflammatory cell infiltration and goblet cell density were evaluated.

Klk13 expression was detected in the cornea, conjunctiva and meibomian glands and was upregulated ~1.8-fold and ~2.5-fold in the cornea and conjunctiva respectively of mice by 10 days post-DS relative to control. Immunohistochemistry also showed increased Klk13 staining in the cornea, conjunctiva, meibomian glands and lacrimal glands of 10 day DS mice compared to controls. Western blot analysis revealed Klk13 protein expression in the conjunctiva, cornea, and lacrimal glands with higher levels in the cornea of mice exposed to DS. Furthermore, western blot analysis demonstrated that antibodies within serum isolated from ALKC mice contained autoantibodies specific for Klk13; however, serum from control mice did not cross-react with recombinant human Klk13.

The inventors also assessed the capacity of CD4+ T cells from klk13-immunized mice to respond to ocular surface antigens present in cornea and conjunctiva of ALKC mice and the ability of Klk13 to exacerbate ALKC in vivo. $CD4^+$ T cells isolated from Klk13-immunized mice in the presence of DS showed a significantly greater proliferative response to DS surface antigens compared to $CD4^+$ T cells from mice exposed to DS alone. Topical challenge with Klk13 without DS was also sufficient to significantly enhance the $CD4^+$ T cell proliferative response to ocular surface antigens in vitro. In addition, DS mice that were topically challenged with Klk13 displayed a marked increase in inflammatory cell infiltration into the conjunctiva that was associated with a significant (50%; $p \leq 0.001$) decrease in goblet cell density relative to control mice or those exposed to DS alone.

These data demonstrate that Klk13 expression is upregulated in tissues of the LFU during ALKC, Klk13 autoantibodies are generated during ALKC, Klk13 potentiates the $CD4^+$ T cell proliferative response to DS antigens and Klk13 exacerbates the severity of ALKC.

Example II

Mouse Model of Dry Eye

C57BL/6 mice of both genders, 6-8 wk old, were purchased from The Jackson Laboratory (Bar Harbor, Me.) and Taconic (Germantown, N.Y.). All animal experiments were approved by the institutional animal care and use committees at Allergan, Inc, and Baylor College of Medicine. All studies adhered to the Association for Research in Vision and Ophthalmology statement for the Use of Animals in Ophthalmic and Vision Research.

Induction of DS in Mice

Desiccating stress (DS) was induced by subcutaneous injection of scopolamine hydrobromide (0.5 mg/0.2 ml; Sigma-Aldrich, St. Louis) three times a day, alternating flanks of mice. Mice were placed in a cage with a perforated plastic screen on one side to allow airflow from a fan placed 6 inches in front of it for 16 h/day. Room humidity was maintained at 30-35%. DS was induced for 5 or 10 consecutive days (DS5 or DS10, respectively). This model of dry eye disease has been used previously with no discernible ill effects from the scopolamine treatment or low humidity. Where indicated, the ocular surface of mice were treated topically with either 5 µl of PBS or Klk13 (1.5 µg/dose) TID throughout the 10 days of DS treatment or hind footpad injected with 10 mg Klk13 in Complete Freud's Adjuvant (CFA) prior to initiation of DS. Control mice were maintained in a nonstressed (NS) environment containing 50-75% relative humidity without exposure to forced air.

Histology and Periodic Acid Schiff Staining

Eyes and ocular adnexa were surgically excised, fixed in 10% formalin, paraffin embedded and 8 µm sections were cut. Sections were stained with periodic-Schiff (PAS) reagent for measuring goblet cell density and were examined and photographed with a microscope equipped with a digital camera (Eclipse E400 with a DS-Fi1; Nikon, Melville, N.Y.). Goblet cell density in the superior and inferior conjunctiva was measured in 3 sections from each eye using image-analysis software (NIS Elements Software, version 3.0, BR, Nikon) and expressed as number of goblet cells per 100 µm.

For immunohistochemistry, the eyes and adnexa of mice/time point (n=5) were excised, embedded in optimal cutting temperature (OCT compound; VWR, Suwanee, Ga.), and flash frozen in liquid nitrogen. Sagittal 8-µm sections were cut with a cryostat (HM 500; Micron, Waldorf, Germany) and placed on glass slides that were stored at −80° C.

Immunohistochemistry

Immunohistochemistry was performed to detect and count the cells in the conjunctival epithelium and stroma that stained positively for CD4 (clone H129.9, 10 ug/mL, BD Bioscience, San Diego, Calif.). Cryosections were stained with the above mentioned primary antibody and appropriate biotinylated secondary antibody (BD Pharmingen) and Vectastain Elite ABC using NovaRed reagents (Vector, Burlingame, Calif.). Secondary antibody alone and appropriate anti-mouse isotype (BD Biosciences) controls were also performed. Three sections from each animal were examined and photographed with a microscope equipped with a digital camera (Eclipse E400 with a DS-Fi1; Nikon). Positively stained cells were counted in the goblet cell rich area of the conjunctiva, over a length of at least 500 µm in the epithelium and to a depth of 75 µm below the epithelial basement membrane in the stroma for a distance of 500 µm using image-analysis software (NIS Elements Software, version 3.0, BR, Nikon).

Immunofluorescent Staining and Laser Scanning Confocal Microscopy

Cryosections dual stained for Klk13 (1:100, 5 ug/mL, Abcam, Cambridge, Mass.) and EGF (R&D Systems, Minneapolis, Minn.) were developed using goat anti-rabbit Alexa-Fluor 488 conjugated IgG and donkey anti-goat 633 antibodies. Negative controls were performed at the same time and consisted of sections incubated with an isotype antibody (BD Pharmingen) or sections with primary antibody omitted. Digital images (512×512 pixels) were captured with a laser-scanning confocal microscope (LSM 510, Zeiss with krypton-argon and He—Ne laser; Zeiss, Thornwood, N.Y.) equipped with 488, 543-nm and 633 nm excitation and BP505-550, BP 560-615 and LP 650 emission filters. They were acquired with a 40/1.3× oil-immersion objective. Images from DS10 and control corneas were captured with identical photomultiplier tube gain settings and processed the same way (LSM-PC software; Carl Zeiss Meditec, Inc.).

Western Blot

Control and 4 week DS C57 mouse conjunctiva, cornea, meibomian gland, and lacrimal gland were processed for total protein using protein extraction kit (Millipore, Billerica, Mass.). Extracted tissue protein was quantified using BCA protein assay (Pierce). One microgram of protein was run on a NuPAGE 4-12% Bis-Tris gel (Invitrogen, Carlsbad, Calif.). Proteins were transferred to PVDF membrane (Invitrogen) by constant 25 Volts, 160 mAmps for 60 min. The membrane was blocked with 5% dry milk in TTBS solution overnight at 4° C. The membrane was washed and incubated with anti-human Klk13 antibody (Abcam 1:1000) at 4° C. overnight. Membrane was washed and incubated with secondary antibody anti-rabbit IgG-HRP (1:1000 dilution) (Amersham GE, Cambridge, Mass.). After final washes, the membrane was processed using the chemiluminescent development system (Amersham GE). Blots were stripped and reprobed with anti-mouse EGF (R&D Systems, Minneapolis, Minn. 4 ng/10 ml/blot) followed by anti-goat IgG HRP (1:1000 dilution) (R&D Systems), and bands were detected with chemiluminescent development system (Amersham GE).

C57BL/6 WT mouse and human serum from normal or dry eye groups were processed on a Zeba desalt spin column (Pierce, Rockford, Ill.). Antibody was then purified using a MelonGel IgG purification kit (Pierce). Recombinant human kallikrein 13 (1 ug per lane) (R&D Systems) was run on a NuPAGE 4-12% Bis-Tris gel (Invitrogen, Carlsbad, Calif.). Proteins from the gel were transferred to PVDF membrane (Invitrogen). The membrane was blocked with 5% dry milk in TTBS solution overnight at 4° C. The membranes were washed and incubated with either antibody purified human serum (1:200 dilution in TTBS, antibody purified mouse serum (1:20 dilution in TTBS), or anti-human Klk13 antibody (Abcam, Cambridge, Mass. 1:10,000 dilution) at 4° C. overnight, membranes were washed and then incubated with secondary antibody with either anti-human IgG-HRP (GE Healthcare, Buckinghamshire, UK NA933V at 1:10,000 dilution), anti-mouse IgG-HRP (Amersham GE NIF825-1:1000 dilution), anti-rabbit IgG-HRP (Amersham GE NIF824-1:1000 dilution), respectively. After final washes, the membrane was incubated with the chemiluminescent substrate (Amersham GE, Niskayuna, N.Y.) for 1 minute.

RNA Isolation and Real Time PCR

Total RNA from the cornea and conjunctiva (individually collected and individually pooled) from NS and DS10 (n=4 samples/time point) was extracted using an acid guanidium thiocyanate-phenol-chloroform method. One sample consisted of pooled samples from 5 mice, per time point. Samples were treated with DNAse to prevent genomic DNA contamination according to the manufacturer's instructions (Qiagen, Valencia, Calif.).

First-strand cDNA was synthesized from 1 µg of total RNA using random hexamers and M-MuLV reverse transcriptase (Ready-To-Go You-Prime First-Strand Beads; GE Healthcare, Inc., Piscataway, N.J.). Real-time PCR was performed using gene expression assay primers and MGB probes specific for murine GAPDH, EGF, Klk13 (Assay IDs: Mm99999915, Mm01316968, Mm01197336, respectively). The GAPDH gene was used as an endogenous reference for each reaction. The results of quantitative PCR were analyzed by the comparative $C_T$ method where target change=$2^{-\Delta\Delta C_t}$. (User Bulletin, No. 2, P/N 4303859; ABI). The cycle threshold (Ct) was determined using the primary (fluorescent) signal as the cycle at which the signal crossed a user-defined threshold. The results were normalized by the $C_t$ value of GAPDH and the mean $C_T$ of relative mRNA level in the nonstressed C57BL/6 group was used as the calibrator.

Co-Culture Assay

Cornea and conjunctiva served as stimulators in the co-culture assay. The corneas and conjunctiva of naïve and DS BALB/c mice were excised and minced into pieces small enough to fit through a 200 µl pipette. To inhibit proliferation of corneal cells, corneas from control (CT) and DS mice were pretreated with 40 µg/ml of mitomycin-C (Sigma-Aldrich, St. Louis, Mo.)) for 30 minutes at 37° C. Mitomycin-C was removed by washing the corneas ten times with DPBS (no calcium and magnesium chloride) (Gibco, Carlsbad, Calif.) prior to co-culturing with purified CD4+ T cells. Spleen and superficial cervical lymph nodes (SCLN) cell suspensions from the different mouse treatment groups were enriched for responder $CD4^+$ T cells using rat anti-mouse CD4-conjugated magnetic microbeads (Miltenyi Biotec, Auburn, Calif.). Isolated cells were found to be >95% $CD4^+$ by flow cytometry. Wedges from one whole cornea were seeded in a 96-well plate together with $5 \times 10^5$ CD4+ T cells/200 µl media/well. Co-cultures were maintained for 4 days at 37° C. and at the end of this period cell proliferation was measured with a WST-based assay. Absorbance readings were recorded using Spectra Max 190 at 440 nm (Molecular Devices, Sunnyvale, Calif.).

Evaluation of Th1 and Th17 Responses

Mice were injected in their hind footpad with Klk13 in CFA at 10 ug/mouse and placed under desiccating stress (DS) for ten days. Control mice received hind footpad injections of CFA. Following ten days of DS treatment, superficial cervical lymph node and spleen CD4+ T cells (responders) were labeled with (spell CFSE) CFSE prior to the assay to track proliferating cells (high CFSE=non proliferating; low CFSE=proliferating) and co-cultured with control or 10 day DS conjunctiva and cornea (one-half/well). For CFSE labeling, the Invitrogen CFDS-SE reagent was reconstituted in DMSO and diluted with 37° C. PBS to a final concentration of 10 M. Cells were incubated with CFSE dye for 15 min at 37° C., washed, and resuspended in 37° C. RPMI media for 30 minutes at 37° C. and then thoroughly washed. Following 4 days of co-culture, cells were gated on low CFSE positive cells (proliferating cells) and assayed for expression of Th1 (T-bet), Th2 (GATA-3) and Th17 (RORγt)-specific transcription factors by intracellular staining and flow cytometry. For intracellular staining, cells were first fixed, treated with 0.1% saponin, and then individually stained with PerCPCy5.5 anti-mouse T-bet (clone eBio4B10), PE anti-mouse Gata-3 (clone TWAJ) or anti-mouse RORγt (clone B2d) followed by biotin conjugated anti-rat IgG and PerCP streptavidin in FACS media containing 0.1% saponin. All of the above antibodies were purchased from eBiosciences (San Diego, Calif.), excluding the PerCP streptavidin which was purchased from BD Pharmingen (San Diego, Calif.) Samples were analyzed on the FACSCalibur (BD Pharmingen).

Statistics

Between group statistical comparisions for goblet cell and $CD4^+$ cell densities were performed using GraphPad Prism software, version 5.0 (GraphPad Software Incorporation, San Diego, Calif.). Multiple group comparisons were done by one way analysis of variance (ANOVA) with Tukey's post hoc testing, $P \leq 0.05$ was considered statistically significant.

Klk13 is Expressed in Cornea, Conjunctiva and Lacrimal Glands

To evaluate if Klk13 is expressed in the LFU, we performed laser scanning confocal microscopy in sections dual labeled for Klk13 and EGF. We noted that in normal, nonstressed conditions, Klk13 is expressed at low levels in the basal layers of the cornea and throughout the entire thickness of the conjunctiva (FIG. 1A) and in the ductal epithelia of the meibomian gland (data not shown). Strong staining was also noted in the lacrimal gland acini. EGF immunoreactivity was noted to co-localize with Klk13 in ocular surface and lacrimal epithelia.

Desiccating Stress Induces Increased Expression of Klk13

Cryosections dual stained for EGF and Klk13 demonstrated that EGF immunoreactivity decreased in cornea and conjunctiva, while Klk13 staining intensity increased in cornea, conjunctiva (FIG. 1A) and meibomian gland (data not shown). Levels of Klk13 mRNA transcripts were noted to increase 1.8-fold and ~2.5-fold in the cornea and conjunctiva, respectively following 10 days of DS relative to control FIG. 1B).

Figure 2:
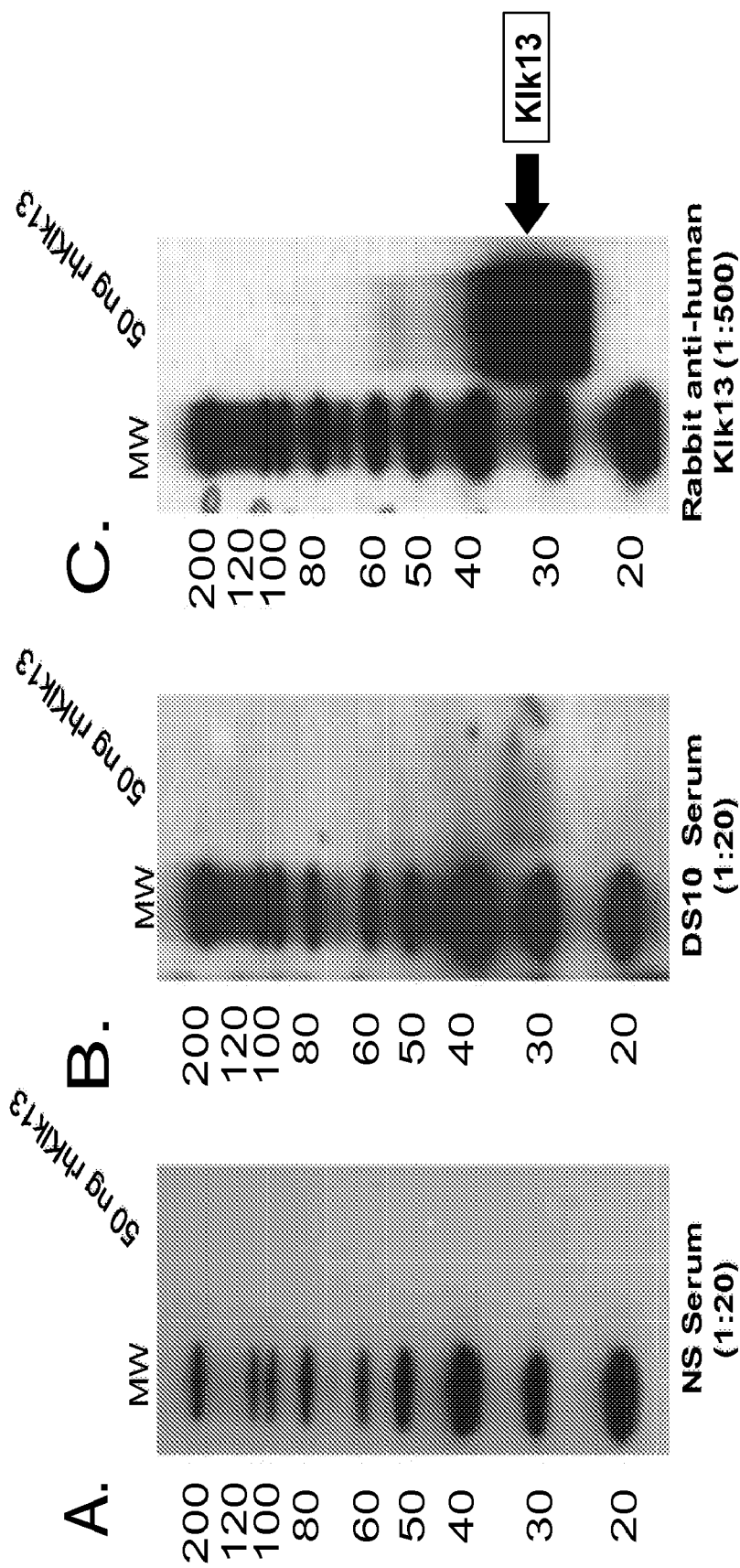

Western blot analysis was also used to semiqualitatively measure Klk13 protein expression in the conjunctiva, cornea, and lacrimal gland before and after exposures to DS (FIG. 1C). The Klk13 antibody recognized a low molecular weight band migrating at ~20 kDa (Klk13 monomer) and a high-weight complex between 60-80 kDa. The presence of the 70 kDa band is consistent with previous studies that showed a high molecular weight complex of Klk13 and EGF (1; 23; 27). Indeed, an anti-EGF antibody detected the presence of EGF in the 70 kDa band containing Klk13, whereas EGF was not detected in the lower-weight band (FIG. 1D). These data show that Klk13 expression is upregulated in the ocular surface tissues of the LFU during desiccating stress and further demonstrates that Klk13 and EGF interact to form a multimer with a predicted stoichiometry of $Klk13_2:EGF_2$. (2) Based on these findings, the inventors contend that DS increases immune exposure of Klk13 protein through increased expression and epitope unmasking due to lower level of EGF binding in the ocular surface tissues of the LFU by 10 days of DS.
DS Stimulates Production of Klk13 Specific Autoantibodies To determine if upregulation of Klk13 within epithelia of the LFU during desiccating stress resulted in an autoantibody response, serum was isolated from control mice or those exposed to DS for 10 days. Western blot analysis demonstrated that antibodies within serum from control mice did not cross-react with recombinant human Klk13 (FIG. 2). In contrast, serum isolated from mice subjected to DS for 10 days contained antibodies specific for Klk13.
Topical Immunization with Klk13 in the Presence of 10 Day DS Results in Reduced conjunctival Goblet Cell Density A significant loss of goblet cells (~50%) was observed in mice exposed to both DS and topical klk13 relative to control mice or those exposed to DS alone (P<0.001). This was accompanied by a significant increase in CD4.sup.+ T cells in goblet cell rich areas compared to the untreated and PBS treated controls (p<0.001) (FIGS. 3A-H). Collectively these data demonstrate that klk13 exacerbates the severity of ALKC.
Immunization with Klk13 Enhances the Proliferative Response of CD4+ T Cells to Ocular Surface Tissues A co-culture experiment with ocular surface tissues and CD4+ T cells was performed to determine the antigenicity of Klk13. C57BL/6 mice were immunized by hind footpad injection with 10 µg Klk13+CFA. CD4+ T cells were isolated from the spleen and superficial cervical lymph nodes of mice treated as i) control, ii) 10 days DS iii) 10 day DS+topical Klk13 (1.5 µg/dose) for 10 days, or topical Klk13 (1.5 µg/dose) for 3 days and mixed with normal or 10 day DS minced conjunctiva and cornea from unstressed control or 10 days DS mice. After 4 days of co-culture, cell proliferation was measured with the WST cell proliferation assay.

Figure 4:
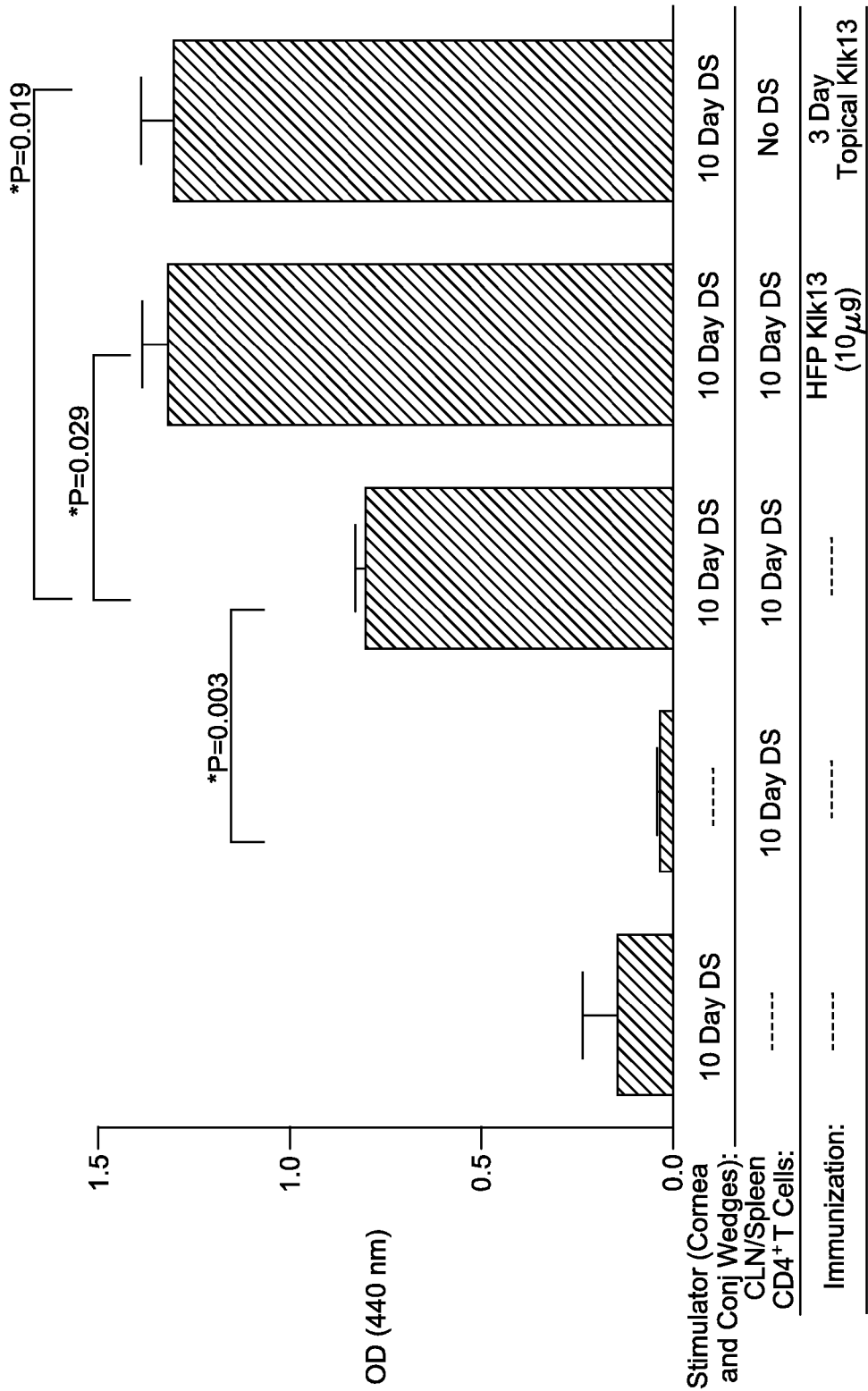

Conjunctival and corneal wedges from DS mice cultured in the presence of 10 day DS $CD4^+$ T cells resulted in a significant increase (*P=0.003) in T cell proliferation relative to DS $CD4^+$ T cells alone. CD4+ T cells isolated from DS mice immunized with Klk13 in the presence or absence of 10 DS showed a significantly greater proliferative response to DS surface antigens compared to the response of 10 day DS $CD4^+$ T cells to DS wedges (*P=0.029) (FIG. 4).
Evaluation of Klk13-Mediated Th1 and Th17 Responses Naïve T cells can differentiate into either Th1 cells (T-bet+), Th2 cells (Gata-3), or Th17 cells (RORγt) positive cells. T-bet, Gata-3, and RORγt are transcription factors that regulate the differentiation of T cells into a particular subset of T cells. Co-culture of control CD4+ T cells with wedges of ocular surface tissues from control nonstressed mice resulted in a small population of low CFSE expressing cells (proliferating) that were GATA-3 positive (3.04%)(data not shown). These results suggest that the normal homeostatic ocular surface is skewed to a low basal Th2 response.

Both T-bet and RORγt positive, CFSE low expressing populations were detected in co-culture with CD4+ T cells from DS (T-bet=5.18%; RORγt=5.62%), DS+CFA (T-bet=7.36%, RORγt=4.94%) and 10 Day DS+klk13 (10 ug)/HFP (T-bet=2.2%; RORγt=4.32%) incubated with DS conjunctiva and cornea wedges for 4 days (FIGS. 5A-C). No GATA-3 detection was observed in any groups in which DS CD4+ T cells were used (data not shown). Elevated Th1 (T-bet) and Th17 (RORγt) expression in proliferating T cells demonstrates that Th1 and Th17 cells are present and ready to respond to antigens in DS conjunctival and corneal wedges.
Human Sjogren's Syndrome Patients Had Increases in Klk13 Transcripts and Autoantibodies Against Klk13

To determine whether human Sjogren's Syndrome (SS) patients produce autoantibodies against klk13, purified IgG antibody from human serum of 20 SS patients and 3 normal patients were individually tested for reactivity to human klk13 by Western blot. Anti-Klk13 antibody was present in 6 out of the 20 SS patients tested (FIGS. 6A and B). Of the 6 patients positive for anti-Klk13 antibody, the ocular surface scores ranged from 5.5-9. Two of the 3 normal patients had ocular surface scores of 0, and these normal patients did not have detectable anti-klk13 antibody. One normal patient had an ocular surface score of 2, and did have detectable levels of anti-Klk13 antibody.
Figure Legends FIG. 1. Laser scanning microscopy of immunostaining of lacrimal gland, cornea and conjunctiva sections dual labeled for klk13 and EGF with propidium iodide counterstaining of non-stressed (NS) and mice subjected to desiccating stress for 10 days (DS10). CN=cornea, CJ=conjunctiva (A). mRNA transcripts of klk13 in cornea, conjunctiva and LG tissues. NS=non-stressed controls, DS10=mice subjected to desiccating stress for 10 days (B). Western blot analysis of klk13 expression in tissues of the LFU (CONJ=conjunctiva, CO=cornea, LG=lacrimal gland). Protein lysates from control (NS) or DS mice were run on SDS-PAGE gel, transferred to nitrocellulose, and immunoblotted with rabbit anti-human klk13 antibody at 1:1000. Increased klk13 monomer protein levels were observed in cornea from DS mice compared to controls. Western blot analysis of conjunctiva tissue with anti-EGF antibody. NS=non-stressed controls, DS10=mice subjected to desiccating stress for 10 days (C).

FIG. 2. Serum was isolated from mice following 10 day exposure to DS and was used to probe 50 ng of recombinant human Klk13 that was previously transferred to nitrocellulose from a SDS-PAGE gel. A) Serum from control mice did not cross-react with Klk13, but B) serum from 10 day DS mice contained antibodies that recognized Klk13. C) Anti-human Klk13 antibody was used as a positive control.

Figure 3:
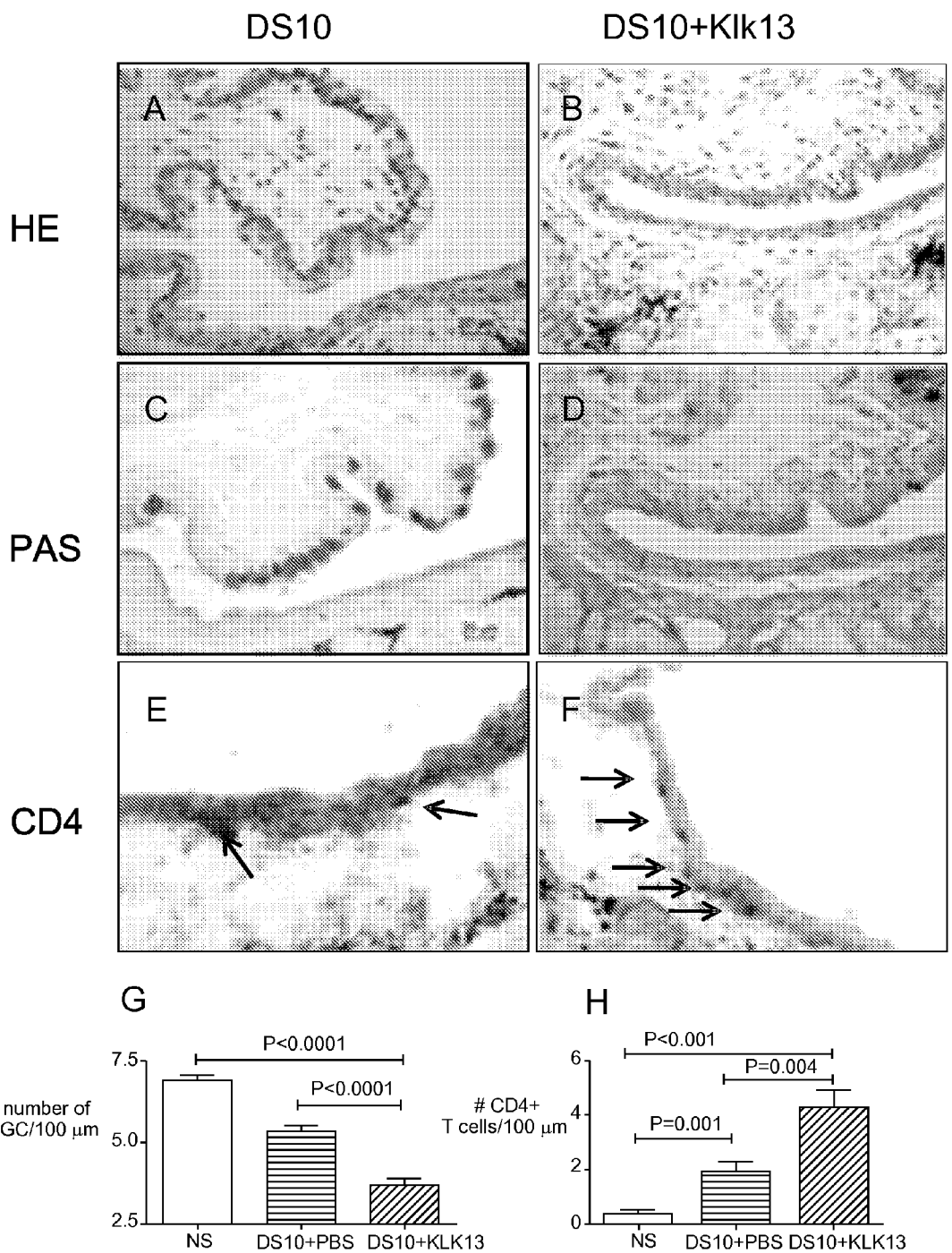

FIG. 3. Topical Klk13 in the presence of 10 day DS results in reduced numbers of goblet cells. To determine if Klk13 contributes to the immunopathogenesis of ALKC, C57BL/6 mice were exposed to DS for 10 days. In addition, mice were topically challenged with i) PBS or ii) Klk13 (1.5 pg/eye/day) for ten days. Exposure to DS in the presence of topical Klk13 resulted in a marked increase in inflammatory cell infiltration into the conjunctiva that was greater than mice exposed to DS alone. A dramatic loss of goblet cells was observed in mice exposed to both DS and topical Klk13 relative to mice exposed to DS alone. Quantification revealed a 50% decrease in goblet cell density within the conjunctiva that was significantly (9<0.001) greater than control and DS mice. There was a significant increase in CD4+ T cells in goblet cell rich areas compared to the untreated and PBS controls.

FIG. 4. Immunization with Klk13 enhances the proliferative response of CD4+ T cells to the ocular surface. Conjunctival and corneal wedges from DS mice cultured in the presence of 10 Day DS CD4+ T cells resulted in a significant increase in T cell proliferation relative to DS CD4+ T cells alone. CD4+ T cells isolated form mice immunized with Klk13 and DS or treated with topical Klk13 showed a significantly greater proliferative response to DS surface antigens. $CD4^+$ T cell responses to control cornea were below 0.2 (OD, nm) regardless of Klk13 immunization. HFP=hind footpad. n=3 wells (mean+/−SEM). Media value was subtracted.

Figure 5:
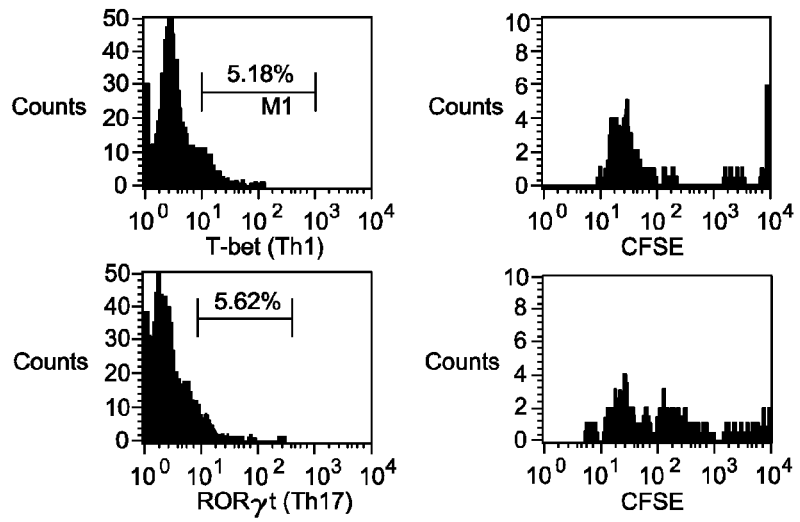
Figure 5:
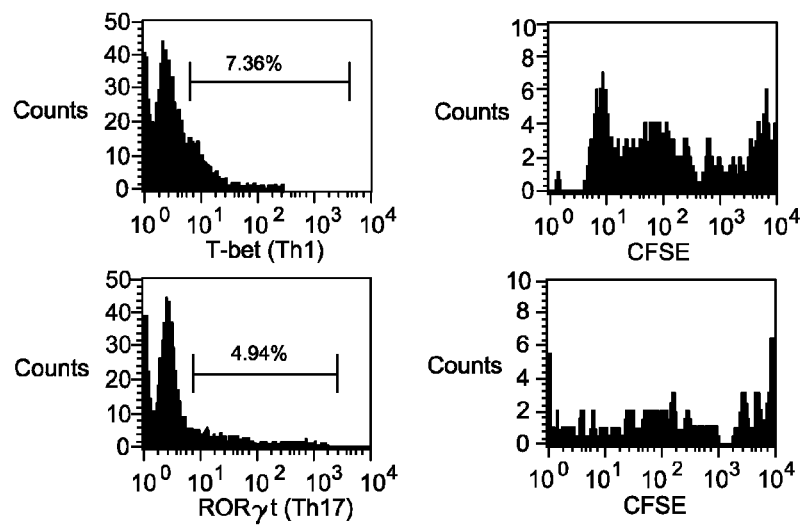
Figure 5:
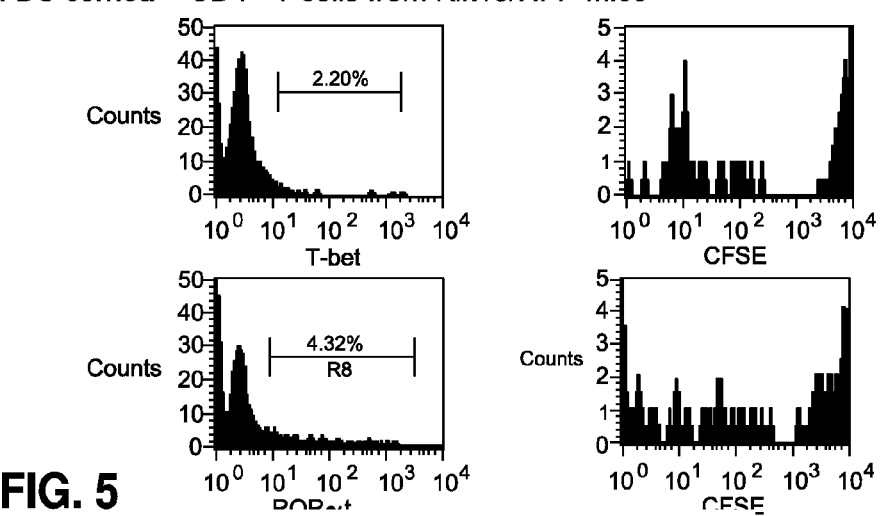

FIG. 5. Proliferating CD4+ T cells in the presence of DS cornea and conjunctiva wedges are T bet and RORγt positive. CD4+ T cells from DS, CFA/HFP, or Klk13/HFP mice were labeled with CFSE and incubated with DS cornea for 4 days. At the end of 4 days, cells were intracellularly stained for T-bet and RORγt. Populations of cells positive for either T-bet or RORγt were gated and these gated populations were analyzed for CFSE expression on a FACSCalibur.

Figure 6:
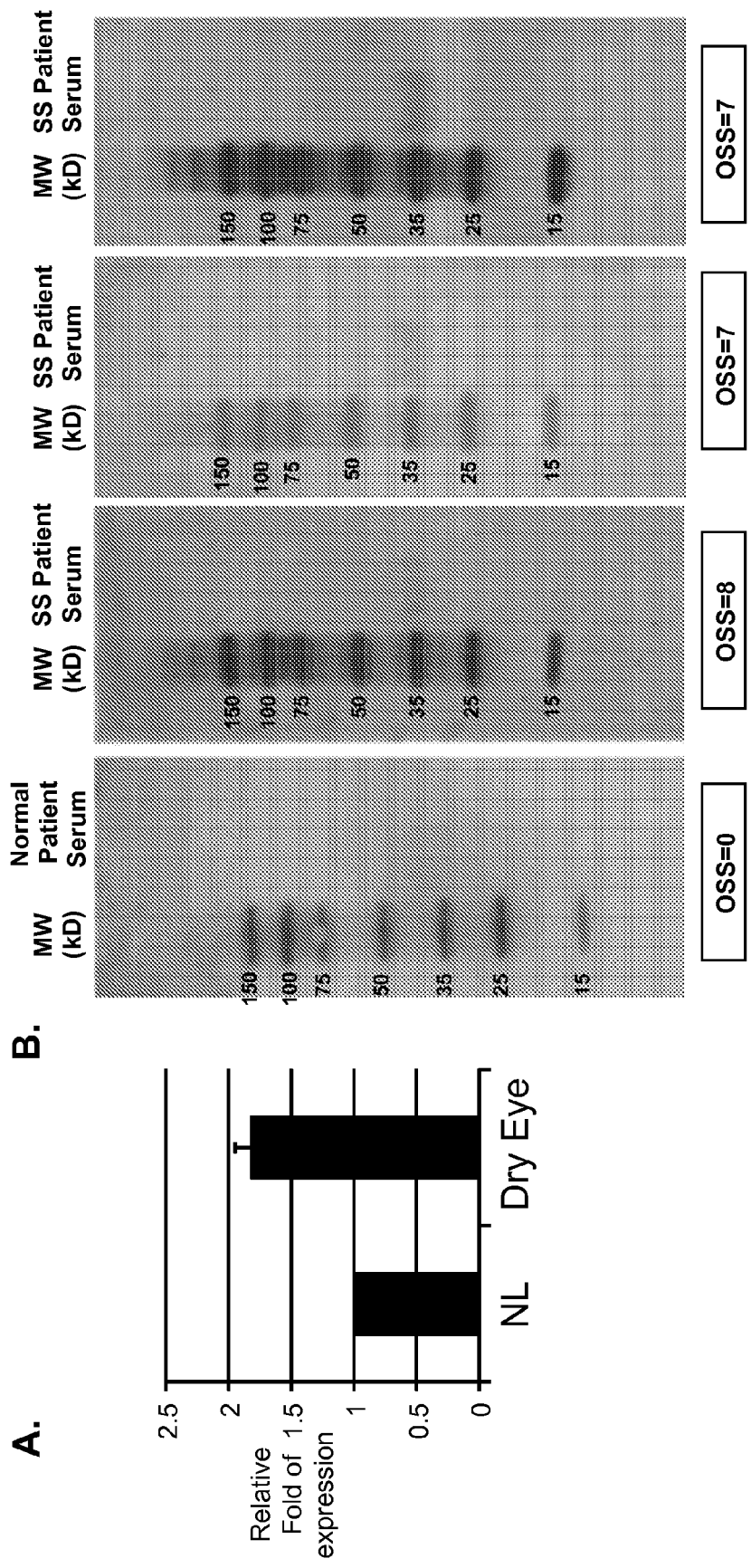

FIG. 6. Sjogren's syndrome patients had increased Klk13 expression and autoantibodies against Klk13. There was a 1.7 fold increase in Klk13 transcripts in Sjogren's syndrome patients (n=4). Western blot analysis of human Klk13 (1 μg) for the presence of autoantibodies against Klk13. Human Klk13 run on an SDS-PAGE gel and transferred to PVDF membrane. Membranes were blotted with anti-IgG purified antibodies from the human serum samples. 6 out of 20 Sjogren's syndrome patients had autoantibodies which recognized human Klk13. One normal patient and 3 Sjogren's syndrome patients are shown. OSS=ocular surface score.

What is claimed is:

1. A method for the treatment of dry eye, the method comprising topically administering to a patient in need of such treatment a pharmaceutical composition comprising an anti-KLK-13 antibody.

2. The method of claim 1, wherein the anti-KLK-13 antibody is a polyclonal, monoclonal, humanized, bispecific, or heteroconjugate antibody, or a functional fragment of the foregoing that binds KLK-13.

* * * * *

UNITED STATES PATENT AND TRADEMARK OFFICE
CERTIFICATE OF CORRECTION

PATENT NO. : 8,211,434 B2
APPLICATION NO. : 13/129436
DATED : July 3, 2012
INVENTOR(S) : Michael E. Stern et al.

It is certified that error appears in the above-identified patent and that said Letters Patent is hereby corrected as shown below:

In column 16, line 44, delete "comparisions" and insert -- comparisons --, therefor.

In column 17, line 34, delete "(-50%)" and insert -- (~50%) --, therefor.

In column 18, line 61, delete "(1.5 pg/eye/day)" and insert -- (1.5 µg/eye/day) --, therefor.

In column 20, line 6, before "run" insert -- was --.

Signed and Sealed this
Fourth Day of September, 2012

David J. Kappos
*Director of the United States Patent and Trademark Office*